United States Patent
Moroz et al.

(10) Patent No.: US 10,564,100 B1
(45) Date of Patent: Feb. 18, 2020

(54) ANALYSIS OF VIABLE AND NONVIABLE CELLS

(71) Applicant: SageMedic Corporation, Redwood City, CA (US)

(72) Inventors: Ekaterina Moroz, Redwood City, CA (US); Christian Apfel, Redwood City, CA (US); Kraig K. Anderson, Redwood City, CA (US)

(73) Assignee: SageMedic Corporation, Redwood City, CA (US)

( * ) Notice: Subject to any disclaimer, the term of this patent is extended or adjusted under 35 U.S.C. 154(b) by 0 days.

(21) Appl. No.: 16/159,482

(22) Filed: Oct. 12, 2018

(51) Int. Cl.
*G01N 21/64* (2006.01)

(52) U.S. Cl.
CPC ..... *G01N 21/6428* (2013.01); *G01N 21/6452* (2013.01); *G01N 21/6458* (2013.01); *G01N 2021/6432* (2013.01); *G01N 2021/6439* (2013.01)

(58) Field of Classification Search
None
See application file for complete search history.

(56) References Cited

U.S. PATENT DOCUMENTS

| | | | | |
|---|---|---|---|---|
| 6,459,805 B1* | 10/2002 | Reynolds | ........... | G01N 21/6428 382/128 |
| 7,202,036 B2* | 4/2007 | Cai | ...................... | C12Q 1/6818 435/6.11 |
| 7,582,483 B2* | 9/2009 | Mizutani | .................. | C12Q 1/02 436/172 |
| 8,993,260 B2* | 3/2015 | Stimpson | ................. | C12Q 1/04 435/34 |
| 9,709,500 B2* | 7/2017 | Wainwright | ....... | G01N 21/6486 |
| 2009/0061477 A1* | 3/2009 | Tibbe | ............... | G01N 33/54326 435/39 |
| 2011/0212481 A1* | 9/2011 | Morgan | ............... | C12N 5/0062 435/29 |
| 2013/0323745 A1* | 12/2013 | Wainwright | ....... | G01N 21/6486 435/6.15 |

* cited by examiner

*Primary Examiner* — Andrae S Allison
(74) *Attorney, Agent, or Firm* — Squire Patton Boggs (US) LLP

(57) ABSTRACT

Provided are methods, for selectively analyzing a cell sample. Viable cells are dyed with a membrane-permeable fluorescent dye, and nonviable cells are dyed with a membrane-impermeable fluorescent quenching dye. The cells are illuminated to cause fluorescent emission from the membrane-permeable fluorescent dye in the viable cells and the membrane-impermeable fluorescent quenching dye in the non-viable cells. The cells are then quenched for at least a portion of fluorescence of the membrane-permeable fluorescent dye in the nonviable cells by the membrane-impermeable fluorescent quenching dye. The cells are then analyzed for viable and nonviable cells.

18 Claims, 2 Drawing Sheets

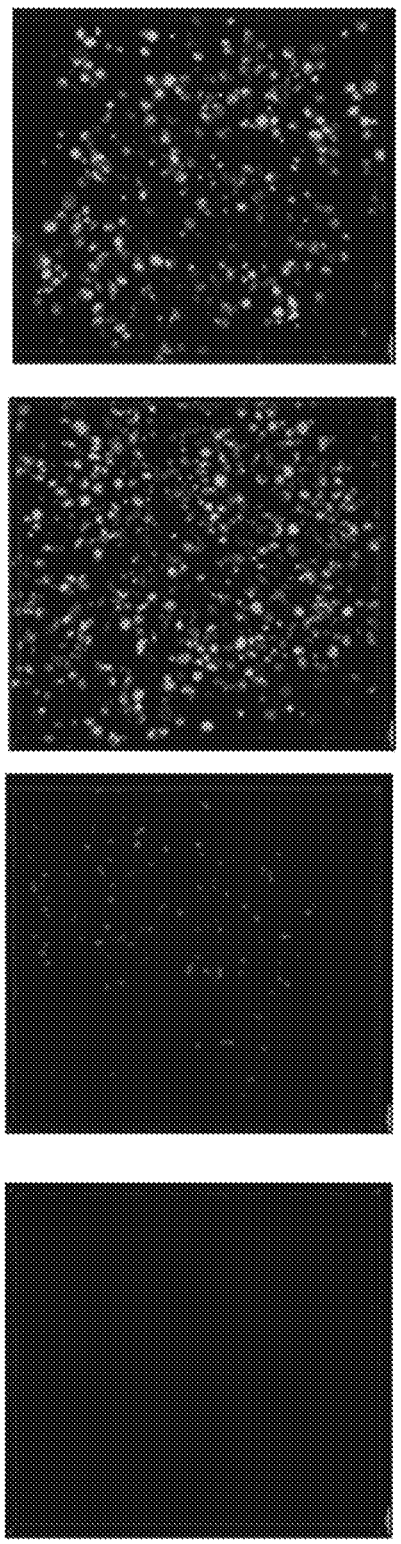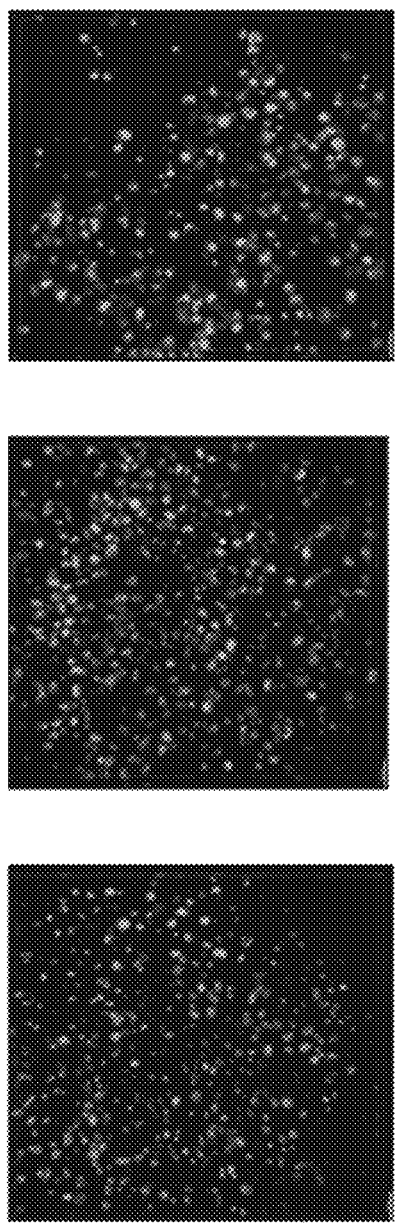

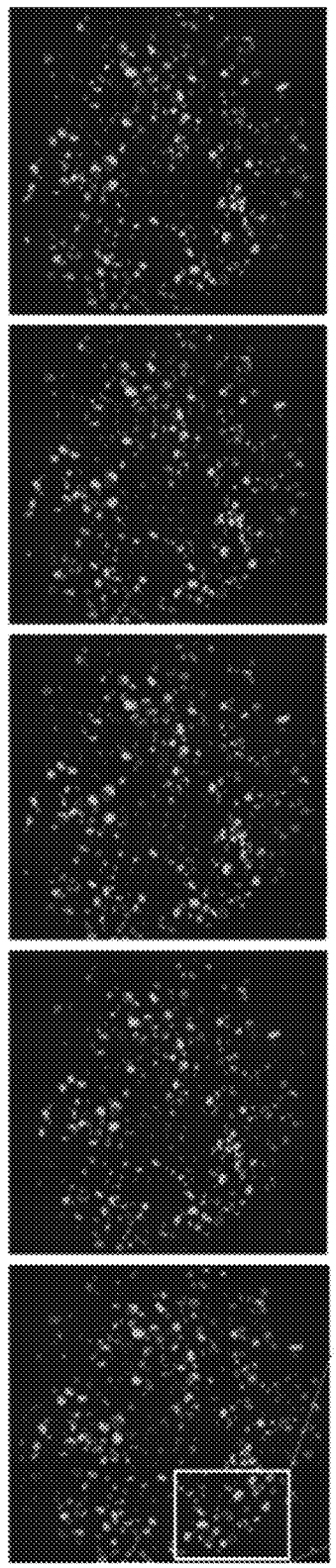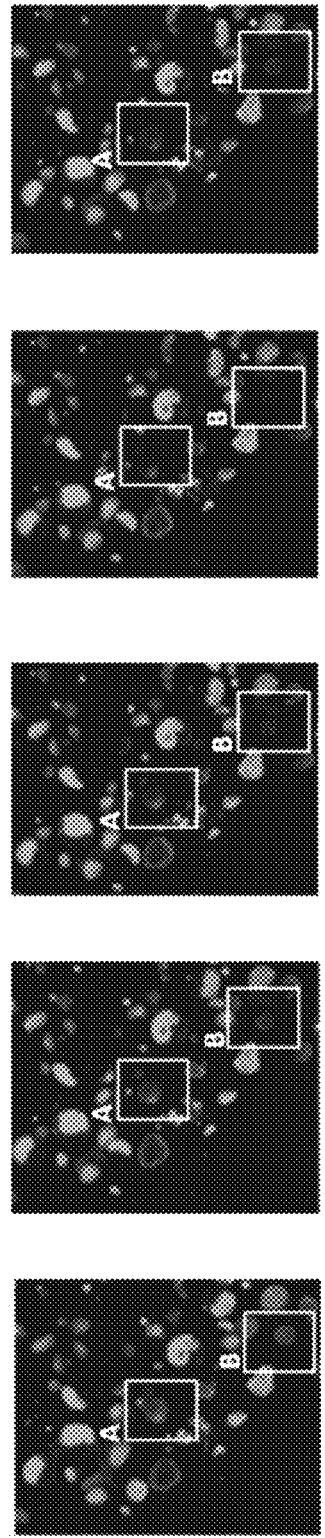

ANALYSIS OF VIABLE AND NONVIABLE CELLS

BACKGROUND

There is current interest in techniques for identifying the presence of cells, e.g., in a sample, such as a cancer biopsy, microbes in body fluids, medical products, foods, and the like. In many situations, it may be desirable to analyze viable (e.g., live) cells and nonviable (e.g., dead) cells. It may also be desirable to distinguish between viable and non-viable cells. Further, it may be desirable to count and/or distinguish such cells simply and quickly.

Traditional cell culture methods for assessing viable and nonviable cells can take hours to days to perform, which can depend upon the organisms that are being tested. Further, in order to separately analyze viable and non-viable cells, complex instrumentation and time-consuming data manipulation may be employed. For example, a variety of systems have been developed that label viable cells with one fluorescent dye and label non-viable cells with both the first dye and a second, different fluorescent dye. To separately analyze the viable and non-viable cells, illumination and detection may use multiple scans using specialized light sources and/or filters to provide and receive selected bands of light. Additionally, the fluorescence received from each dye may be manipulated in software to separately view the viable cells from the non-viable cells.

Viability dyes are known that may be activated within viable cells, for example, by metabolic activity (e.g., esterase cleavage of ester functionalized pro-fluorophores) within the cells. The fluorescent background may be reduced by using a membrane-impermeable quencher, but in such an approach, only the viable cells are detected. Some fluorescent dyes are membrane-impermeable and preferentially label non-viable cells over viable cells. Some systems employ a combination of one or more membrane-permeable dyes, one or more quenchers, and one or more membrane-impermeable dyes. However, increasing amounts of the various dyes and quenchers may undesirably perturb the behavior of viable cells or even kill them, and may also increase the generation of hazardous waste.

The present application appreciates that conducting fluorescent cell-based assays may be a challenging endeavor.

SUMMARY OF THE INVENTION

In various embodiments, a method is provided for selectively analyzing a sample for viable cells and nonviable cells. The method may include providing a sample that includes one or more viable cells and/or one or more nonviable cells. The method may include contacting the sample with a membrane-permeable fluorescent dye and a membrane-impermeable fluorescent quenching dye. The fluorescent cell-dyeing conditions may be effective to cause the one or more viable cells and/or the one or more nonviable cells to be dyed by the membrane-permeable fluorescent dye. The fluorescent cell-dyeing conditions may be effective to cause the one or more nonviable cells to be dyed with the membrane-impermeable fluorescent quenching dye. The membrane-permeable fluorescent dye may be characterized by a first fluorescent excitation band and a first fluorescence emission band. The membrane-impermeable fluorescent quenching dye may be characterized by a second fluorescent excitation band and a second fluorescence emission band. The method may include illuminating the sample under conditions effective to cause emitting of the first fluorescence emission band from the one or more viable cells dyed by the membrane-permeable fluorescent dye. The method may include illuminating the sample under conditions effective to cause emitting of the second fluorescence emission band from the one or more nonviable cells dyed by the membrane-impermeable fluorescent quenching dye. The method may include illuminating the sample under conditions effective to cause quenching of at least a portion of fluorescence of the membrane-permeable fluorescent dye in the one or more nonviable cells by the membrane-impermeable fluorescent quenching dye. The method may include selectively analyzing the sample for: a presence of the one or more viable cells according to the first fluorescence emission band and/or a presence of the one or more nonviable cells according to the second fluorescence emission band.

In various embodiments, a composition is provided. The composition may include a membrane-permeable fluorescent dye. The membrane-permeable dye may be characterized by a first fluorescent excitation band and a first fluorescence emission band. The composition may include a membrane-impermeable fluorescent quenching dye. The membrane-impermeable fluorescent quenching dye may be characterized by a second fluorescent excitation band and a second fluorescence emission band.

In various embodiments, a kit for selectively analyzing a sample for viable cells and nonviable cells is provided. The kit may include a composition. The composition may include a membrane-permeable fluorescent dye. The membrane-permeable dye may be characterized by a first fluorescent excitation band and a first fluorescence emission band. The composition may include a membrane-impermeable fluorescent quenching dye. The membrane-impermeable fluorescent quenching dye may be characterized by a second fluorescent excitation band and a second fluorescence emission band. The kit may include instructions. The instructions may direct a user to provide a sample comprising one or more viable cells and/or one or more nonviable cells. The instructions may direct a user to contact the sample with the composition. The one or more viable cells and/or the one or more nonviable cells may be dyed by the membrane-permeable fluorescent dye. The one or more nonviable cells may be dyed with the membrane-impermeable fluorescent quenching dye. The instructions may direct a user to illuminate the sample under conditions effective to cause emitting of the first fluorescence emission band from the one or more viable cells dyed by the membrane-permeable fluorescent dye. The instructions may direct a user to illuminate the sample under conditions effective to cause emitting of the second fluorescence emission band from the one or more nonviable cells dyed by the membrane-impermeable fluorescent quenching dye. The instructions may direct a user to illuminate the sample under conditions effective to cause quenching of at least a portion of fluorescence of the membrane-permeable fluorescent dye in the one or more nonviable cells by the membrane-impermeable fluorescent quenching dye. The instructions may direct the user to selectively analyze the sample for: a presence of the one or more viable cells according to the first fluorescence emission band and/or a presence of the one or more nonviable cells according to the second fluorescence emission band.

Various features, aspects, and advantages of the present invention will become more apparent from the following detailed description of preferred embodiments of the invention, along with the accompanying drawings in which like numerals represent like components.

BRIEF DESCRIPTION OF THE FIGURES

FIG. 1A is a confocal fluorescent microscopy image of a sample prepared by incubation with a membrane-impermeable fluorescent quenching dye for 30 min followed by addition of the masking agent and incubation for an additional 1 h.

FIG. 1B is a confocal fluorescent microscopy image of a sample prepared by incubation with the membrane-impermeable fluorescent quenching dye for 30 min.

FIG. 1C is a confocal fluorescent microscopy image of a sample prepared by incubation with the membrane-impermeable fluorescent quenching dye for 30 min, followed by addition of a membrane-permeable fluorescent dye and incubation for an additional 1 h.

FIG. 1D is a confocal fluorescent microscopy image of a sample incubated with the membrane-impermeable fluorescent quenching dye for 30 min, followed by addition of the membrane-permeable fluorescent dye and masking reagent and incubation for an additional 1 h.

FIG. 1E is a confocal fluorescent microscopy image of a sample prepared by incubation with the membrane-permeable fluorescent dye alone for 1 h.

FIG. 1F is a confocal fluorescent microscopy image of a sample prepared by incubation with the membrane-permeable fluorescent dye alone for 1 h, followed by addition of the membrane-impermeable fluorescent quenching dye and incubation for an additional 30 min.

FIG. 1G is a confocal fluorescent microscopy image of a sample prepared by incubation with the membrane-permeable fluorescent dye and masking reagent for 1 h, followed by addition of the membrane-impermeable fluorescent quenching dye and incubation for an additional 30 min.

FIGS. 2A & 2B are confocal fluorescent microscopy images of a sample prepared by incubation with the membrane-permeable fluorescent dye, taken immediately after addition of the membrane-impermeable fluorescent quenching dye. FIG. 2B is an enlargement of the indicated section of FIG. 2A.

FIGS. 2C & 2D are confocal fluorescent microscopy images of a sample prepared by incubation with the membrane-permeable fluorescent dye, taken 5 min after addition of the membrane-impermeable fluorescent quenching dye. FIG. 2D is an enlargement of the indicated section of FIG. 2C.

FIGS. 2E & 2F are confocal fluorescent microscopy images of a sample prepared by incubation with the membrane-permeable fluorescent dye, taken 20 min after addition of the membrane-impermeable fluorescent quenching dye. FIG. 2F is an enlargement of the indicated section of FIG. 2E.

FIGS. 2G & 2H are confocal fluorescent microscopy images of a sample prepared by incubation with the membrane-permeable fluorescent dye, taken 30 min after addition of the membrane-impermeable fluorescent quenching dye. FIG. 2H is an enlargement of the indicated section of FIG. 2G.

FIGS. 2I & 2J are confocal fluorescent microscopy images of a sample prepared by incubation with the membrane-permeable fluorescent dye, taken 45 min after addition of the membrane-impermeable fluorescent quenching dye. FIG. 2J is an enlargement of the indicated section of FIG. 2I.

DETAILED DESCRIPTION

This document relates generally to a method, composition and kit capable of selectively analyzing, e.g., detecting and distinguishing a presence of viable and/or nonviable cells in a cell sample. The method, composition, and kit may distinguish viable and non-viable cells using only two dyes, a membrane-permeable fluorescent dye and a membrane-impermeable fluorescent quencher. The method, composition, and kit may distinguish viable and non-viable cells using broad-band illumination, without the need for lasers or other specialized, filtered light sources. The method, composition, and kit may distinguish viable and non-viable cells using a single image, e.g., a fluorescence microscope image, without requiring separate scans or deconvolution in software. The method, composition, and kit may distinguish viable and non-viable cells using dyeing methods that are effective within less than two hours. In particular, this document describes a method, composition and kit for detecting viable cells in a cell sample using a membrane-permeable fluorescent dye that permeates both viable and non-viable cells, and a membrane-impermeable fluorescent quenching dye that selectively permeates non-viable cells. Under suitable illumination, the membrane-permeable fluorescent label may exhibit fluorescence in the viable cells. In the nonviable cells, under the suitable illumination, the membrane-impermeable fluorescent quenching dye may quench at least a portion of fluorescence by the membrane-permeable fluorescent dye and the membrane-impermeable fluorescent quenching dye may itself exhibit fluorescence. Accordingly, the viable and non-viable cells may both be detected, and may be distinguished according to fluorescence in the viable cells of the membrane-permeable fluorescent dye and fluorescence in the nonviable cells by the membrane-impermeable fluorescent quenching dye.

In various embodiments, a method is provided for selectively analyzing a sample for viable cells and nonviable cells. The method may include providing a sample that includes or is suspected to include one or more viable cells and/or one or more nonviable cells. The method may include contacting the sample with a membrane-permeable fluorescent dye and a membrane-impermeable fluorescent quenching dye under fluorescent cell-dyeing conditions. The fluorescent cell-dyeing conditions may be effective to cause the one or more viable cells and/or the one or more nonviable cells to be dyed by the membrane-permeable fluorescent dye. The fluorescent cell-dyeing conditions may be effective to cause the one or more nonviable cells to be dyed with the membrane-impermeable fluorescent quenching dye.

The membrane-permeable fluorescent dye may be characterized by a first fluorescent excitation band and a first fluorescence emission band. The membrane-impermeable fluorescent quenching dye may be characterized by a second fluorescent excitation band and a second fluorescence emission band. The first fluorescent excitation band may be distinct from the second fluorescent excitation band. The first fluorescent emission band may be distinct from the second fluorescent emission band. The first fluorescent emission band may overlap the second fluorescent excitation band.

The method may include illuminating the sample under conditions effective to cause emitting of the first fluorescence emission band from the one or more viable cells dyed by the membrane-permeable fluorescent dye. The method may include illuminating the sample under conditions effective to cause emitting of the second fluorescence emission band from the one or more nonviable cells dyed by the membrane-impermeable fluorescent quenching dye. The method may include illuminating the sample under conditions effective to cause quenching of at least a portion of fluorescence of the membrane-permeable fluorescent dye in the one or more nonviable cells by the membrane-impermeable fluorescent quenching dye. The method may include selectively analyzing the sample for: a presence of the one or more viable cells according to the first fluorescence emission band and/or a presence of the one or more nonviable cells according to the second fluorescence emission band.

In some embodiments, the sample may include no viable cells. The sample may include no nonviable cells. The sample may include no viable cells and no nonviable cells. The sample may include at least one cell, viable or nonviable.

In some embodiments, the method may include selectively analyzing the sample. Selectively analyzing the sample may include detecting a number of the one or more viable cells present in the sample. The number of the one or more viable cells present in the sample may be, for example, 1, 5, 10, 15, 20, 25, 50, 75, 100, 150, 200, 250, 500, 750, 1,000, 1,250, 1,500, 1,750, 2,000, 2,500, 5,000, 7,500, 10,000, or a range between any two of the preceding values, for example, between about 1-10,000, 1-1,000, 1-500, 1-250, 1-100, and the like. Selectively analyzing the sample may include detecting a number of the one or more nonviable cells present in the sample. The number of the one or more nonviable cells present in the sample may be, for example, 1, 5, 10, 15, 20, 25, 50, 75, 100, 150, 200, 250, 500, 750, 1,000, 1,250, 1,500, 1,750, 2,000, 2,500, 5,000, 7,500, 10,000, or a range between any two of the preceding values, for example, between about 1-10,000, 1-1,000, 1-500, 1-250, 1-100, and the like. Selectively analyzing the sample may include detecting the presence of a plurality of the one or more viable cells. Selectively analyzing the sample may include detecting the presence of a plurality the one or more nonviable cells.

In several embodiments, illuminating the sample may include selectively illuminating in the first excitation band corresponding to the membrane-permeable fluorescent dye. Illuminating the sample may include selectively illuminating in the second excitation band corresponding to the membrane-impermeable fluorescent quenching dye. Selectively illuminating may include, for each excitation band, using a corresponding light source that is selective for each excitation band, each corresponding light source comprising one or more of: a laser, a light emitting diode, and a filtered broadband light source. Illuminating the sample may include contacting the sample with broad-band illumination. The broad-band illumination may overlap the first excitation band corresponding to the membrane-permeable fluorescent dye. The broad-band illumination may overlap the second excitation band corresponding to the membrane-impermeable fluorescent quenching dye.

In some embodiments, selectively analyzing the sample for the one or more viable cells and/or the one or more nonviable cells may include filtering light emitted from the sample using a first emission filter that is selective for the first fluorescence emission band. Selectively analyzing the sample for the one or more viable cells and/or the one or more nonviable cells may include filtering light emitted from the sample using a second emission filter that is selective for the second fluorescence emission band.

Selectively analyzing the sample may include analyzing light emitted from the sample simultaneously for the first fluorescence emission band and the second fluorescence emission band. The method may include distinguishing the one or more viable cells and/or the one or more nonviable cells according to a spectral difference between the first fluorescence emission band and the second fluorescence emission band.

Selectively analyzing the sample for the one or more viable cells and/or the one or more nonviable cells may include acquiring an image of the sample using light emitted by the first fluorescence emission band and the second fluorescence emission band. Selectively analyzing the sample for the one or more viable cells and/or the one or more nonviable cells may include distinguishing the one or more viable cells and/or the one or more nonviable cells in the image according to a first color corresponding to the first fluorescence emission band and a second color corresponding to the second fluorescence emission band.

Selectively analyzing the sample for the one or more viable cells and/or the one or more nonviable cells may include acquiring an image of the sample using light emitted by the first fluorescence emission band and the second fluorescence emission band. Selectively analyzing the sample for the one or more viable cells and/or the one or more nonviable cells may include determining a number of the one or more viable cells in the image according to light emitted by the first fluorescence emission band, and a number of the one or more nonviable cells in the image according to light emitted by the second fluorescence emission band. Selectively analyzing the sample for the one or more viable cells may include determining a number of the one or more viable cells in the image by counting cells and/or cell nuclei corresponding to the first fluorescence emission band. Selectively analyzing the sample for the one or more nonviable cells may include determining a number of the one or more nonviable cells in the image by counting cells and/or cell nuclei corresponding to the second fluorescence emission band.

In various embodiments, the illumination may include a wavelength in nanometers (nm) of one of about 350, 400, 450, 500, 550, 600, 650, 700, 750, 800, 850, 900, 950, or 1000, or a range between about any two of the preceding values, for example, 350-1000 nm, 350-400 nm, 350-450 nm, 350-500 nm, 350-550 nm, 350-600 nm, 400-450 nm, 400-500 nm, 400-550 nm, 400-600 nm, 400-650 nm, 450-500 nm, 450-550 nm, 450-600 nm, 450-650 nm, 450-700 nm, 500-550 nm, 500-600 nm, 500-650 nm, 500-700 nm, 500-750 nm, 550-600 nm, 550-650 nm, 550-700 nm, 550-750 nm, 550-800 nm, 600-650 nm, 600-700 nm, 600-750 nm, 600-800 nm, 600-850 nm, 650-700 nm, 650-750 nm, 650-800 nm, 650-850 nm, 650-900 nm, 700-750 nm, 700-800 nm, 700-850 nm, 700-900 nm, 700-950 nm, 750-800 nm, 750-850 nm, 750-900 nm, 750-950 nm, 750-1000 nm, and the like.

In some embodiments, each fluorescent emission band can be detected at a wavelength in nanometers (nm) of one of about 350, 400, 450, 500, 550, 600, 650, 700, 750, 800, 850, 900, 950, or 1000, or a range between about any two of the preceding values, for example, 350-1000 nm, 350-400 nm, 350-450 nm, 350-500 nm, 350-550 nm, 350-600 nm, 400-450 nm, 400-500 nm, 400-550 nm, 400-600 nm, 400-650 nm, 450-500 nm, 450-550 nm, 450-600 nm, 450-650 nm, 450-700 nm, 500-550 nm, 500-600 nm, 500-650 nm, 500-700 nm, 500-750 nm, 550-600 nm, 550-650 nm, 550-700 nm, 550-750 nm, 550-800 nm, 600-650 nm, 600-700 nm, 600-750 nm, 600-800 nm, 600-850 nm, 650-700 nm, 650-750 nm, 650-800 nm, 650-850 nm, 650-900 nm, 700-750 nm, 700-800 nm, 700-850 nm, 700-900 nm, 700-950 nm, 750-800 nm, 750-850 nm, 750-900 nm, 750-950 nm, 750-1000 nm, and the like.

Illuminating and selectively analyzing the sample may include using one or more of any fluorescence analysis technique or fluorescence analytical device known to the art, for example, one or more of: fluorescence imaging, fluorescence spectroscopy, fluorescence imaging microscopy, epifluorescence microscopy, confocal fluorescence imaging microscopy, a fluorometer, a fluorescence microplate reader, fluorescence flow cytometry, and the like.

In various embodiments, the method may include providing the sample in a cell culture device. The cell culture device may include, for example, at least one of: a multiwell plate, a multiwell strip, an optical cell, and a flow cytometry apparatus.

The cell culture device may include a chamber or conduit for liquid, such as a well, an optical cell, a culture dish, a microtiter plate, a cuvette, a capillary tube, a flow cell, a flow cytometry apparatus, and the like. The cell culture device may include a solid support, for example, a microscope slide or a filter surface. The cell culture device may include a material selected to be substantially free of autofluorescence when exposed to light having a wavelength in the range from about 350 nm to about 1000 nm, or in a subrange corresponding to the excitation bands of the membrane-permeable dye and the membrane-impermeable dye. Suitable substrates that are non auto-fluorescent in at least some wavelength ranges of interest may include, e.g., glass, quartz, sapphire, polystyrene, a nylon, nitrocellulose, polycarbonate, polyacrylic acid, poly(methyl methacrylate) (PMMA), polyester, polysulfone, polytetrafluoroethylene (PTFE), polyethylene, polypropylene, and the like.

The cell culture device may include at least one window. Illuminating the sample may be conducted through the at least one window. Selectively analyzing the sample may be conducted through the at least one window. The cell culture device may include at least one optically flat window. Selectively analyzing the sample may include using any fluorescence analysis technique or fluorescence analytical device known to the art, for example, fluorescence imaging, fluorescence spectroscopy, fluorescence imaging microscopy, epifluorescence microscopy, confocal fluorescence imaging microscopy, a fluorometer, a fluorescence microplate reader, fluorescence flow cytometry, and the like. For example, selectively analyzing the sample may include, for example, conducting confocal fluorescence imaging microscopy of the sample through the at least one optically flat imaging window.

In several embodiments, the method may include culturing the one or more viable cells in the sample under cell culture conditions. The cell culture conditions may include a temperature in ° C. of about one of: 20, 21, 22, 23, 24, 25, 26, 27, 28, 29, 30, 31, 32, 33, 34, 35, 36, 37, 38, 39, or 40, or a range between any two of the preceding values, for example, between about 20-40° C., 25-40° C., 30-40° C., 35-40° C., and the like. The cell culture conditions may include a pH value of one of about: 6, 6.25, 6.5, 6.6, 6.7, 6.8, 6.9, 7, 7.1, 7.2, 7.3, 7.4, 7.5, 7.6, 7.7, 7.8, 7.9, or 8, or a range between about any two of the preceding values, for example, pH 6-8, pH 7-8, pH7-7.6, pH 7.3-7.5, and the like. The cell culture conditions may include a presence of a cell culture medium. The cell culture medium may include, for example, water, salt, a buffer, nutrients, and the like. The cell culture medium may include, for example, serum, e.g., fetal bovine serum, human serum, autologous serum from a subject from which the sample and cells are derived, and the like. For example, human primary tumor cells may be cultured in serum derived from the human subject from whom the human primary tumor cells were derived.

Culturing the sample under cell culture conditions may permit growth and/or proliferation of the viable cells. The viable and non-viable cells may be further analyzed by standard procedures, for example, amplification procedures including polymerase chain reaction, ligase chain reaction, rolling circle replication, and the like, and nucleic acid sequencing.

Selectively analyzing the sample may be conducted at two or more points in time to determine, for example, a presence or absence of a change in the one or more viable cells and/or the one or more nonviable cells. For example, selectively analyzing the sample may be conducted at two or more points in time to determine a presence or an absence of a change in a number of the one or more viable cells and/or a number of the one or more nonviable cells.

In some embodiments, the method may include contacting the sample with at least one agent. The method may include selectively analyzing the sample, including selectively analyzing the one or more viable cells and/or the one or more nonviable cells for a presence or an absence of a change in response to the at least one agent. The method may include selectively analyzing the presence or the absence of the response with respect to an overall sample concentration of the at least one agent. The method may include selectively analyzing the presence or the absence of the response with respect to a concentration gradient in the sample. The method may include selectively analyzing the presence or the absence of the response with respect to a time variation of the overall sample concentration. The method may include selectively analyzing the presence or the absence of the response with respect to a time variation of the concentration gradient in the sample.

In various embodiments, the at least one agent may include, for example, a gas, a metabolite, a nutrient, a biomolecule, an acid, a base, a buffer, a salt, and a therapeutic drug. For example, the at least one agent may include an anticancer agent, a therapeutic drug used as an adjunct in cancer therapy, a compound suspected of modulating cancer therapy, or the like. The at least one agent may include an adjuvant therapy, for example, one or more of: supraphysiological temperature, radiation, subphysiological temperature, sonotherapy, and electrochemotherapy.

In some embodiments, the sample may include a three-dimensional micro-tissue formed of a plurality of cells, e.g., the one or more viable cells and/or the one or more nonviable cells. The cells may be, for example, prokaryotic cells or eukaryotic cells. The method may be used to determine the number of viable cells and non-viable cells in at least a portion of the sample, for example, a liquid sample. The liquid sample may be, for example, a water sample, an ingestible fluid, e.g., wine, beer, milk, baby formula or the like, a body fluid, e.g., blood, lymph, urine, lung interstitial fluid, cerebrospinal fluid or the like), growth media, a liquid sample produced by harvesting cells from a source of interest, e.g., via a biopsy. The sample may include prokaryotic cells. The sample may include eukaryotic cells. The sample may include mammalian cells. The sample may include human cells. The sample may include cancer cells, e.g., from a cancer cell line. The sample may include cancer cells from a subject, e.g., primary tumor cells. The sample may include cells of a patient-derived cancer cell xenograft. The sample may include primary tumor cells from a single human subject. The sample may include cells grown in a xenograft of primary cells derived from a single human subject.

In several embodiments, the method may include contacting the sample with the membrane-permeable fluorescent dye before the membrane-impermeable fluorescent quenching dye. The method may include contacting the sample with the membrane-permeable fluorescent dye after the membrane-impermeable fluorescent quenching dye. The method may include contacting the sample with the membrane-permeable fluorescent dye at the same time as the membrane-impermeable fluorescent quenching dye. The method may include contacting the sample with a composition comprising the membrane-permeable fluorescent dye together with the membrane-impermeable fluorescent quenching dye.

In various embodiments, the membrane-permeable fluorescent dye and the membrane-impermeable fluorescent quenching dye may be cell-structure selective dyes. For example, the membrane-permeable fluorescent dye and the membrane-impermeable fluorescent quenching dye may be nucleic acid binding dyes. In certain embodiments, the membrane-permeable fluorescent dye and the membrane-impermeable fluorescent quenching dye may bind to one another, e.g., in the non-viable cells.

The method may include contacting the sample with an amount of the membrane-impermeable fluorescent quenching dye, e.g. compared to an amount of the membrane-permeable fluorescent dye, effective to provide the quenching of at least a portion of fluorescence of the membrane-permeable fluorescent dye in the one or more nonviable cells. The amount of the membrane-impermeable fluorescent quenching dye may be effective to substantially quench fluorescence of the membrane-permeable fluorescent dye in the one or more nonviable cells. The amount of the membrane-impermeable fluorescent quenching dye may be effective to quench fluorescence of the membrane-permeable fluorescent dye in the one or more nonviable cells by a percentage of the unquenched fluorescence of at least about one of: 50, 75, 80, 85, 90, 95, 96, 97, 98, 99, 99.5, 99.6, 99.7, 99.8, 99.9, 99.95, 99.99, 99.995, 99.999, 99.9995, 99.9999, 100, and the like, or a range between any two of the preceding values, for example, between about 95% and 100%, 99%, and 100%, and the like.

In some embodiments, the first fluorescent emission band may be characterized by an overlap with an excitation band of the membrane-impermeable fluorescent quenching dye. The overlap may be effective to provide the quenching of at least a portion of fluorescence of the membrane-permeable fluorescent dye in the one or more nonviable cells by the membrane-impermeable fluorescent quenching dye. The overlap may be effective to provide resonant energy transfer from an excited state of the membrane-permeable fluorescent dye to a ground state of the membrane-impermeable fluorescent quenching dye. Without wishing to be bound by theory, the resonant energy transfer may be radiationless, e.g., as known to the art under the term Föerster resonant energy transfer.

In various embodiments, the membrane-permeable fluorescent dye may be selected from Table 1. The membrane-impermeable fluorescent quenching dye may be selected from Table 2. A pair of dyes may be used including a membrane-permeable fluorescent dye selected from Table I and a membrane-impermeable fluorescent quenching dye selected from Table II (all dyes available from Thermo Fisher Scientific, Waltham, Mass.). A pair of dyes may be used including any pair of dyes (a), (b), (c), (d), or (x) as indicated in Table III. A pair of dyes may be used including any pair of dyes (a), (b), (c), or (d) as indicated in Table III. A pair of dyes may be used including any pair of dyes (a), (b), or (c) as indicated in Table III. A pair of dyes may be used including any pair of dyes (a) or (b) as indicated in Table III. A pair of dyes may be used including any pair of dyes (a) indicated in Table III. A pair of dyes may be used including any pair of dyes (b) indicated in Table III. A pair of dyes may be used including any pair of dyes (c) indicated in Table III. A pair of dyes may be used including any pair of dyes (d) indicated in Table III. A pair of dyes may be used including any pair of dyes (x) indicated in Table III.

In various embodiments, a composition is provided. The composition may include a membrane-permeable fluorescent dye. The membrane-permeable dye may be characterized by a first fluorescent excitation band and a first fluorescence emission band. The composition may include a membrane-impermeable fluorescent quenching dye. The membrane-impermeable fluorescent quenching dye may be characterized by a second fluorescent excitation band and a second fluorescence emission band.

In some embodiments, the membrane-permeable fluorescent dye and the membrane-impermeable fluorescent quenching dye may be cell-structure selective dyes. For example, the membrane-permeable fluorescent dye and the membrane-impermeable fluorescent quenching dye may be nucleic acid binding dyes.

TABLE 1

Membrane Permeable Fluorescent Dyes

| # | Dye | excitation $\lambda_{max}$ | emission $\lambda_{max}$ |
|---|---|---|---|
| p1 | Acridine Orange | 502 | 525 |
| p2 | Hoechst 33258 | 355 | 465 |
| p3 | Hoechst 33342 | 355 | 465 |
| p4 | VYBRANT ™ DYECYCLE ™ Violet | 369 | 437 |
| p5 | VYBRANT ™ DYECYCLE ™ Green | 506 | 534 |
| p6 | VYBRANT ™ DYECYCLE ™ Orange | 519 | 563 |
| p7 | VYBRANT ™ DYECYCLE ™ Ruby | 638 | 686 |
| p8 | DRAQ5 ™ | 488, 647 | 697 |
| p9 | CyQUANT ® GR | 501 | 521 |
| p10 | SYTO ™ 40 | 422 | 447 |
| p11 | SYTO ™ 41 | 425 | 452 |
| p12 | SYTO ™ 42 | 436 | 470 |
| p13 | SYTO ™ 43 | 443 | 465 |
| p14 | SYTO ™ 44 | 449 | 475 |
| p15 | SYTO ™ 45 | 451 | 484 |
| p16 | SYTO ™ 9 | 485 | 498 |
| p17 | SYTO ™ 11 | 508 | 527 |
| p18 | SYTO ™ 13 | 488 | 509 |
| p19 | SYTO ™ 14 | 517 | 549 |
| p20 | SYTO ™ 16 | 488 | 518 |
| p21 | SYTO ™ 80 | 531 | 545 |
| p22 | SYTO ™ 81 | 530 | 544 |
| p23 | SYTO ™ 82 | 541 | 560 |
| p24 | SYTO ™ 83 | 543 | 559 |
| p25 | SYTO ™ 84 | 567 | 582 |
| p26 | SYTO ™ 85 | 567 | 583 |
| p27 | SYTO ™ 17 | 621 | 634 |
| p28 | SYTO ™ 59 | 622 | 645 |
| p29 | SYTO ™ 60 | 652 | 678 |
| p30 | SYTO ™ 61 | 628 | 645 |
| p31 | SYTO ™ 62 | 652 | 676 |

TABLE 2

Membrane Impermeable Fluorescent Quenching Dyes

| # | Name | CAS | excitation $\lambda_{max}$ | emission $\lambda_{max}$ |
|---|---|---|---|---|
| q1 | 4',6-diamidino-2-phenylindole (DAPI) | 28718-90-3 | 358 | 461 |
| q2 | Ethidium bromide | 1239-45-8 | 300, 360 | 590 |

TABLE 2-continued

Membrane Impermeable Fluorescent Quenching Dyes

| # | Name | CAS | excitation $\lambda_{max}$ | emission $\lambda_{max}$ |
|---|---|---|---|---|
| q3 | Propidium Iodide | 25535-16-4 | 493 | 636 |
| q4 | 7AAD (7-amino actinomycin D) | 7240-37-1 | 546 | 647 |
| q5 | SYTOX ™ blue | 396077-00-2 | 444 | 480 |
| q6 | SYTOX ™ green | 194100-76-0 | 504 | 523 |
| q7 | SYTOX ™ orange | 324767-53-5 | 547 | 570 |
| q8 | SYTOX ™ red | — | 640 | 658 |
| q9 | POPO ™-1 | 169454-15-3 | 434 | 456 |
| q10 | BOBO ™-1 | 169454-13-1 | 462 | 481 |
| q11 | YOYO ™-1 | 143413-85-8 | 491 | 509 |
| q12 | TOTO ™-1 | 143413-84-7 | 514 | 533 |
| q13 | JOJO ™-1 | 305801-87-0 | 529 | 545 |
| q14 | POPO ™-3 | 154757-99-0 | 534 | 570 |
| q15 | BOBO ™-3 | 169454-17-5 | 570 | 602 |
| q16 | YOYO ™-3 | 156312-20-8 | 612 | 631 |
| q17 | TOTO ™-3 | 166196-17-4 | 642 | 660 |
| q18 | DRAQ7 ™ | 1533453-55-2 | 599, 644 | 678 |

TABLE 3

Pairs of Membrane Permeable Fluorescent Dye/Membrane Impermeable Fluorescent Quenching Dye

| | q1 | q2 | q3 | q4 | q5 | q6 | q7 | q8 | q9 | q10 | q11 | q12 | q13 | q14 | q15 | q16 | q17 | q18 |
|---|---|---|---|---|---|---|---|---|---|---|---|---|---|---|---|---|---|---|
| p1 | x | a | a | a | x | x | b | c | x | x | x | d | a | a | b | c | d | b |
| p2 | x | b | c | b | d | b | c | d | x | b | b | c | c | b | c | c | d | d |
| p3 | x | b | c | b | d | b | c | d | x | x | x | d | c | b | c | c | d | d |
| p4 | x | b | c | c | b | c | c | d | b | b | c | d | c | b | d | d | d | d |
| p5 | x | a | c | a | d | x | a | c | x | x | x | x | a | a | b | c | c | b |
| p6 | x | b | d | b | x | x | x | c | x | x | x | x | c | a | c | c | c | a |
| p7 | x | x | x | x | x | x | x | x | x | x | x | x | x | x | x | x | x | x |
| p8 | x | x | x | x | x | x | x | x | x | x | x | x | x | x | x | x | x | x |
| p9 | x | a | c | a | x | x | b | d | x | x | d | b | a | b | c | c | d | b |
| p10 | x | c | c | c | b | c | d | d | d | b | b | c | c | b | c | d | d | x |
| p11 | x | c | c | c | c | c | d | d | x | a | b | c | c | c | d | d | d | x |
| p12 | x | b | c | b | x | b | c | d | x | b | b | c | c | c | d | d | d | d |
| p13 | x | b | c | b | x | b | c | d | x | c | c | c | c | c | c | d | d | d |
| p14 | x | b | c | b | x | b | c | d | x | d | c | b | c | c | c | d | d | d |
| p15 | x | b | c | b | x | b | c | c | x | x | c | b | c | b | c | c | d | d |
| p16 | x | a | b | a | x | a | c | d | x | x | x | b | c | b | c | c | d | d |
| p17 | x | a | b | a | x | x | b | c | x | x | x | x | a | a | b | b | c | c |
| p18 | x | a | b | a | x | b | b | c | x | x | x | a | b | b | c | c | d | d |
| p19 | x | a | b | a | x | x | b | c | x | x | x | d | a | a | b | b | c | c |
| p20 | x | a | b | a | x | d | b | c | x | x | x | b | a | a | b | c | c | c |
| p21 | x | x | x | c | x | x | x | b | x | x | x | x | x | x | x | b | b | a |
| p22 | x | c | c | b | x | x | x | b | x | x | x | x | x | b | a | b | c | c |
| p23 | x | c | c | a | x | x | x | c | x | x | x | x | c | a | c | d | b |   |
| p24 | x | d | d | b | x | x | x | c | x | x | x | x | x | a | c | d | b |   |
| p25 | x | x | x | x | x | x | x | x | x | x | x | x | x | x | x | x | x | b |
| p26 | x | d | d | c | x | x | x | c | x | x | x | x | x | c | b | b | a |   |
| p27 | x | x | x | x | x | x | x | a | x | x | x | x | x | x | x | x | a | b |
| p28 | x | x | x | x | x | x | x | a | x | x | x | x | x | x | x | x | a | b |
| p29 | x | x | x | x | x | x | x | x | x | x | x | x | x | x | x | x | x | x |
| p30 | x | x | x | x | x | x | x | c | x | x | x | x | x | x | x | x | d | b |
| p31 | x | x | x | x | x | x | x | x | x | x | x | x | x | x | x | x | x | x |

In several embodiments, the composition may be characterized by the membrane-impermeable fluorescent quenching dye and the membrane-permeable fluorescent dye in respective amounts effective to provide quenching of fluorescence of the membrane-permeable fluorescent dye by the membrane-impermeable fluorescent quenching dye under illumination conditions effective to cause one or more of: excitation of the first fluorescent excitation band, emission of the first fluorescence emission band, excitation of the second fluorescent excitation band, and emission of the first fluorescence emission band. The membrane-impermeable fluorescent quenching dye and the membrane-permeable fluorescent dye may be in respective amounts effective to provide substantial quenching of fluorescence of the membrane-permeable fluorescent dye by the membrane-impermeable fluorescent quenching dye under illumination conditions effective to cause one or more of: excitation of the first fluorescent excitation band, emission of the first fluorescence emission band, excitation of the second fluorescent excitation band, and emission of the first fluorescence emission band. The amount of the membrane-impermeable fluorescent quenching dye may be effective to quench fluorescence of the membrane-permeable fluorescent dye under the illumination conditions, e.g., in the one or more nonviable cells, by a percentage of the unquenched fluorescence of at least about one of: 50, 75, 80, 85, 90, 95, 96, 97, 98, 99, 99.5, 99.6, 99.7, 99.8, 99.9, 99.95, 99.99, 99.995, 99.999, 99.9995, 99.9999, 100, and the like, or a range between any two of the preceding values, for example, between about 95% and 100%, 99%, and 100%, and the like.

Without wishing to be bound by theory, the membrane-impermeable fluorescent quenching dyes described may quench fluorescence from the membrane-permeable fluorescent dye by either photo-induced electron transfer (PET), sometimes referred to as static quenching, or Föerster resonance energy transfer (FRET), or some combination thereof. The quenching efficiency may be distance-dependent. Conditions may be selected to facilitate quenching.

For example, the membrane-permeable fluorescent dye and the membrane-impermeable fluorescent quenching dye may be selected such that the first fluorescent emission band overlaps with the second excitation band effective to provide quenching of at least a portion of fluorescence of the membrane-permeable fluorescent dye by the membrane-impermeable fluorescent quenching dye, e.g., under fluorescent cell-dyeing conditions. The overlap may be effective to provide resonant energy transfer from an excited state of the membrane-permeable fluorescent dye to a ground state of the membrane-impermeable fluorescent quenching dye. Without wishing to be bound by theory, the resonant energy transfer may be radiationless, e.g., as known to the art under the term Föerster resonant energy transfer.

For example, the fluorescent membrane-permeable fluorescent dye/membrane-impermeable fluorescent quenching dye pairs may be selected to have a binding affinity for one another, for example, via electrostatic and/or hydrophobic interactions, which may bind to form a substantially quenched non-fluorescent ground-state complex, e.g., in the non-viable cells. The membrane-impermeable quencher may be excluded by the membrane of the viable cells so the non-fluorescent complex may be excluded from viable cells.

Further, for example, the fluorescent membrane-permeable fluorescent dye and/or membrane-impermeable fluorescent quenching dye may be selected for binding affinities for a cellular component, organelle, or structure, such as nucleic acids. When the fluorescent membrane-permeable fluorescent dye and membrane-impermeable fluorescent quenching dye are co-bound to a specific target, such as a nucleic acid in a non-viable cell, the proximity of the dye and quencher may facilitate formation of a substantially quenched, non-fluorescent complex. The membrane-impermeable quencher may be excluded by the membrane of the viable cells so the non-fluorescent complex may be excluded from viable cells.

In various embodiments, the membrane-permeable fluorescent dye may be selected from Table 1. The membrane-impermeable fluorescent quenching dye may be selected from Table 2. A pair of dyes may be used including a membrane-permeable fluorescent dye selected from Table I and a membrane-impermeable fluorescent quenching dye selected from Table II. A pair of dyes may be used including any pair of dyes (a), (b), (c), (d), or (x) as indicated in Table III. A pair of dyes may be used including any pair of dyes (a), (b), (c), or (d) as indicated in Table III. A pair of dyes may be used including any pair of dyes (a), (b), or (c) as indicated in Table III. A pair of dyes may be used including any pair of dyes (a) or (b) as indicated in Table III. A pair of dyes may be used including any pair of dyes (a) indicated in Table III. A pair of dyes may be used including any pair of dyes (b) indicated in Table III. A pair of dyes may be used including any pair of dyes (c) indicated in Table III. A pair of dyes may be used including any pair of dyes (d) indicated in Table III. A pair of dyes may be used including any pair of dyes (x) indicated in Table III.

In various embodiments, the composition may include a physiologically acceptable buffer selected to maintain a pH value. The cell culture conditions may include a pH value of one of about: 6, 6.25, 6.5, 6.6, 6.7, 6.8, 6.9, 7, 7.1, 7.2, 7.3, 7.4, 7.5, 7.6, 7.7, 7.8, 7.9, or 8, or a range between about any two of the preceding values, for example, pH 6-8, pH 7-8, pH7-7.6, pH 7.3-7.5, and the like. The composition may include a cell culture medium. The cell culture medium may include, for example, water, salt, a buffer, nutrients, and the like. The cell culture medium may include, for example, serum, e.g., fetal bovine serum, human serum, autologous serum from a subject from which the sample and cells are derived, and the like. For example, human primary tumor cells may be cultured in serum derived from the human subject from whom the human primary tumor cells were derived. The composition may include one or more of: a gas, a metabolite, a nutrient, a biomolecule, an acid, a base, a buffer, a salt, and a therapeutic drug. The composition may include one or more of: an anticancer agent, a therapeutic drug used as an adjunct in cancer therapy, a compound suspected of modulating cancer therapy, or the like.

In various embodiments, a kit for selectively analyzing a sample for viable cells and nonviable cells is provided. The kit may include a composition. The composition may include a membrane-permeable fluorescent dye. The membrane-permeable dye may be characterized by a first fluorescent excitation band and a first fluorescence emission band. The composition may include a membrane-impermeable fluorescent quenching dye. The membrane-impermeable fluorescent quenching dye may be characterized by a second fluorescent excitation band and a second fluorescence emission band. The kit may include instructions. The instructions may direct a user to provide a sample comprising one or more viable cells and/or one or more nonviable cells. The instructions may direct a user to contact the sample with the composition. The one or more viable cells and/or the one or more nonviable cells may be dyed by the membrane-permeable fluorescent dye. The one or more nonviable cells may be dyed with the membrane-impermeable fluorescent quenching dye. The instructions may direct a user to illuminate the sample under conditions effective to cause emitting of the first fluorescence emission band from the one or more viable cells dyed by the membrane-permeable fluorescent dye. The instructions may direct a user to illuminate the sample under conditions effective to cause emitting of the second fluorescence emission band from the one or more nonviable cells dyed by the membrane-impermeable fluorescent quenching dye. The instructions may direct a user to illuminate the sample under conditions effective to cause quenching of at least a portion of fluorescence of the membrane-permeable fluorescent dye in the one or more nonviable cells by the membrane-impermeable fluorescent quenching dye. The instructions may direct the user to selectively analyze the sample for: a presence of the one or more viable cells according to the first fluorescence emission band and/or a presence of the one or more nonviable cells according to the second fluorescence emission band.

In various embodiments, the kit may include instructions to direct the user to conduct any aspect of the method described herein. The kit may include any aspect of the composition described herein.

EXAMPLES

The invention may be readily understood by reference to the following examples, which are included merely for purposes of illustration of certain aspects and embodiments of the present invention, and are not intended to limit the scope of the invention in any way.

Example 1

A 96 round bottom well plate was seeded with a single cell suspension of about 2,500 ovarian cancer primary tumor cells/20 μl/well at day 0. In each well, 80 μl of DMEM/2% alpha serum was added on top to the total volume of 100 μl/well. Dyes were prepared at 2-fold the desired final concentrations on the day of imaging. At day 3, 100 μL of dyeing mix was carefully added to each well to avoid disturbing the cells, to a final 1-fold concentration of dyes. Cells were incubated with dyes at 37° C. For this example, the dyes used were a membrane-permeable fluorescent dye (CYQUANT® GR, Thermo Fisher Scientific, Waltham, Mass.) and a membrane-impermeable fluorescent quenching dye (DRAQ7™, Thermo Fisher Scientific, Waltham, Mass.).

The following dye combinations and sequences of dye addition were tested in triplicates, and similar results were seen among the triplicates. FIGS. 1A-1G show exemplary results of the dye combination and addition sequences, as follows.

FIG. 1A is a confocal fluorescent microscopy image of a sample prepared by incubation with the membrane-impermeable fluorescent quenching dye for 30 min followed by addition of the masking agent (Diammonium 5-[(E)-(4-acetamido-2-sulfonatophenyl)diazenyl]-6-amino-4-hydroxy-2-naphthalenesulfonate, CAS Reg. No. 302912-22-7, Thermo Fischer Scientific, Waltham, Mass.) and incubation for an additional 1 h. Under conventional confocal fluorescent microscopy conditions used for imaging cells, no signal was observed.

FIG. 1B is a confocal fluorescent microscopy image of a sample prepared by incubation with the membrane-impermeable fluorescent quenching dye for 30 min. Under conventional confocal fluorescent microscopy conditions used for imaging cells, discrete red signals were observed, consistent with dyeing of nonviable cells.

FIG. 1C is a confocal fluorescent microscopy image of a sample prepared by incubation with the membrane-impermeable fluorescent quenching dye for 30 min, followed by addition of the membrane-permeable fluorescent dye and incubation for an additional 1 h. Under conventional confocal fluorescent microscopy conditions used for imaging cells, discrete red signals were observed, consistent with dyeing of nonviable cells, as were discrete green signals, consistent with dyeing of viable cells.

FIG. 1D is a confocal fluorescent microscopy image of a sample prepared by incubation with the membrane-impermeable fluorescent quenching dye for 30 min, followed by addition of the membrane-permeable fluorescent dye and masking reagent and incubation for an additional 1 h. Under conventional confocal fluorescent microscopy conditions used for imaging cells, discrete green signals were observed, consistent with dyeing of viable cells. No red signal was observed, consistent with permeation of the nonviable cells with the masking agent and blocking/quenching of the membrane-impermeable fluorescent quenching dye and the membrane-permeable fluorescent dye signal from the nonviable cells.

FIG. 1E is a confocal fluorescent microscopy image of a sample prepared by incubation with the membrane-permeable fluorescent dye alone for 1 h. Under conventional confocal fluorescent microscopy conditions used for imaging cells, discrete green signals were observed, consistent with dyeing of viable cells. FIG. 1E is comparable to FIG. 1D, where a masking agent was added to block fluorescence from nonviable cells.

FIG. 1F is a confocal fluorescent microscopy image of a sample prepared by incubation with the membrane-permeable fluorescent dye alone for 1 h, followed by addition of the membrane-impermeable fluorescent quenching dye and incubation for an additional 30 min. Under conventional confocal fluorescent microscopy conditions used for imaging cells, discrete red signals were observed, consistent with dyeing of nonviable cells, as were discrete green signals, consistent with dyeing of viable cells. FIG. 1F is comparable to FIG. 1C.

FIG. 1G is a confocal fluorescent microscopy image of a sample prepared by incubation with the membrane-permeable fluorescent dye and masking reagent for 1 h, followed by addition of the membrane-impermeable fluorescent quenching dye and incubation for an additional 30 min. Under conventional confocal fluorescent microscopy conditions used for imaging cells, discrete green signals were observed, consistent with dyeing of viable cells. No red signal was observed, consistent with permeation of the nonviable cells with the masking agent and blocking/quenching of the membrane-impermeable fluorescent quenching dye signal. FIG. 1D is comparable to FIGS. 1D and 1E.

Discussion

The membrane-permeable fluorescent dye alone dyed both viable and nonviable cells. The addition of masking agent also appeared to block fluorescence from the membrane-permeable dye in nonviable cells. The masking agent also appeared to block fluorescence from the membrane-impermeable fluorescent dye in nonviable cells. Further the masking agent appeared to visually reduce a portion of fluorescence associated with the membrane-permeable fluorescent dye in the viable cells.

When the membrane-impermeable fluorescent quenching dye was combined with the membrane-permeable fluorescent dye, fluorescence from the membrane-permeable fluorescent dye disappeared from the nonviable cells regardless of the order of dye addition. After sufficient time, the nonviable cells were only positive for the membrane-impermeable fluorescent quenching dye, with no visible fluorescence from the membrane-permeable fluorescent dye, which was confirmed by the fluorescence intensities quantification for both dyes present in the nonviable cells.

Example 2

In order to further examine the dyeing behavior and kinetics of the membrane-impermeable fluorescent quenching dye and the membrane-permeable fluorescent dye of Example 1 when mixed together, an additional experiment was performed on day 7 of culture as follows.

On day 7, 20 µL of the membrane-permeable fluorescent dye was added at 6× concentration to each well. The cells were incubated with dye at 37° C. for 1 hour. Confocal fluorescent microscopy was performed after incubation. About 20 µL of the membrane-impermeable fluorescent quenching dye was added directly to the same well on the stage at 6× concentration without disturbing the cells.

Dynamic confocal fluorescent microscopy images were taken of the cells immediately after addition of the membrane-impermeable fluorescent quenching dye (FIG. 2A, 2B), as well as at 5 min (FIG. 2C, 2D), 20 min (FIG. 2E, 2F), 30 min (FIG. 2G, 2H) and 45 min (FIG. 2I, 2J) after addition.

The lower images (FIGS. B, D, F, H, & J) of each pair of images shows a zoomed in view of the dyed cells in the upper images (FIGS. A, C, E, G, & I). In the portion of each of FIGS. B, D, F, H, & J indicated by the white boxes, cells that were originally dyed with the membrane-permeable fluorescent dye (green) begin to become red (positive for the membrane-impermeable fluorescent quenching dye), which is visually noticeable after 20-30 minutes. The brightest images in terms of fluorescence intensity was acquired at 45 minutes after addition of the dye (FIG. 2I, 2J). Fluorescence intensity values demonstrated an increase over time of the membrane-impermeable fluorescent quenching dye intensity, accompanied by a corresponding significant decrease over time in the membrane-permeable fluorescent dye fluorescence.

By the 45 min, there was negligible membrane-permeable fluorescent dyeing of the nonviable cells and the nonviable cells were positive for the membrane-impermeable fluorescent quenching dye.

Discussion

Without wishing to be bound by theory, the images of Example 2 are consistent with displacement and/or quenching of the membrane-permeable fluorescent dye by the membrane-impermeable fluorescent quenching dye within the nonviable cells. These results are consistent with analysis of the experiment on day 4 (Example 1) in which the nonviable cells no longer exhibited fluorescence associated with the membrane-permeable fluorescent dye. The result of these examples demonstrates selective, mutually exclusive fluorescent dyeing of the viable and nonviable cells by the membrane-permeable fluorescent dye and the membrane-impermeable fluorescent quenching dye, respectively.

The disclosure of the present application includes several embodiments, which may share common properties and features. The properties and features of one embodiment may be combined with properties and features of other embodiments. Similarly, a single property or feature or combination of properties or features in any embodiment may constitute a further embodiment.

Recitation of ranges of values herein are intended to illustrate each separate value falling within the range, and unless otherwise indicated herein, each individual value is incorporated into the specification as if it were individually recited herein.

The term "about" refers to a range of values of plus or minus 20% of a specified value. For example, the phrase "about 200" includes plus or minus 20% of 200, or from 160 to 240, unless specifically indicated otherwise or contradicted by context.

Ranges may be expressed herein as from "about" or "approximately" one particular value to "about" or "approximately" another particular value. When such a range is expressed, another embodiment includes between each such pair of particular values. Similarly, when values are expressed as approximations, by use of the antecedent "about" or "approximate" it will be understood that each particular value forms another embodiment.

It is understood that the endpoints of each of the ranges are significant both in relation to the other endpoint and independently of the other endpoint. It is also understood that there are a number of values disclosed, wherein each value is also disclosed as "about" that particular value in addition to the value itself. For example, if the value "10" is disclosed, then "about 10" is also disclosed. It is also understood that when a value is disclosed that is "less than or equal to the value" or "greater than or equal to the value" possible ranges between these values are also disclosed, as appropriately understood by the expert with ordinary skills in the art. For example, if the value "10" is disclosed the "less than or equal to 10" as well as "greater than or equal to 10" is also disclosed.

All methods described herein can be performed in any suitable order unless otherwise indicated herein or otherwise clearly contradicted by context. Units, prefixes, and symbols are denoted in their Systéme International de Unites (SI) accepted form unless otherwise specified.

The following terms, as used herein, have the meanings ascribed to them unless specified otherwise.

As used herein, the term "administering" means the introduction of a composition into a container, well, cell, or tissue culture medium, or (as appropriate) onto cells, tissues or surfaces. Such methods are well-known in the art. Any and all methods of introducing the composition are contemplated and the invention is not dependent on any particular means of introduction.

As used herein, the terms "agent" and "compound" are used interchangeably and mean any chemical compound, for example, a macromolecule or a small molecule disclosed herein. The agent may be naturally occurring (e.g. a herb or a natural product), non-naturally occurring, synthetic, purified, recombinant, and the like. An agent may be used alone or in combination with other agents in the methods described herein.

As used herein, a "micro-tissue" means a small aggregation of biological cells, which may include any cells described herein, e.g., viable cells, nonviable cells, cancer cells, primary tumor cells, human cells, human primary tumor cells, and the like. In various embodiments the number of cells in a micro-tissue is less than about one of: 1,000,000, 100,000, 10,000, 1,000, 750, 500, 250, 200, 150, 125, 100, 75, 50, or 25, or a range between any two of the preceding values, for example, 25-1,000 cells, 25-500 cells, 25-150 cells, and the like.

As used herein, "primary tissue" means tissue that was directly removed from an organism, for example by fine needle biopsy, core needle biopsy, or surgical biopsy, typically without further modification. "Primary tumor cells" are cells obtained from primary tissue in a particular subject, by contrast with cancer cells from a cancer cell line.

As used herein, "live primary tissue" means primary tissue in which some cells are alive. As used herein, "cell suspension" and "tissue suspension" may include cells, cell aggregates, tissue fragments, or other biological material suspended in an aqueous solution.

The invention claimed is:

1. A method for selectively analyzing a three dimensional micro-tissue sample for viable cells and nonviable cells, comprising:

providing a sample comprising one or more viable cells and/or one or more nonviable cells; wherein the sample comprises a three-dimensional micro-tissue formed of a plurality of one or more viable cells and/or one or more nonviable cells, and wherein the sample is in a cell culture device comprising a window, the window allowing selective analysis of the sample, the selective analysis comprising conducting confocal fluorescence imaging microscopy of the sample through the window;

contacting the sample with a membrane-permeable fluorescent dye and a membrane-impermeable fluorescent quenching dye, the contacting effective to cause: the one or more viable cells and/or the one or more nonviable cells to be dyed by the membrane-permeable fluorescent dye, and the one or more nonviable cells to be dyed with the membrane-impermeable fluorescent quenching dye, the membrane-permeable fluorescent dye characterized by a first fluorescent excitation band and a first fluorescence emission band and the membrane-impermeable fluorescent quenching dye characterized by a second fluorescent excitation band and a second fluorescence emission band; and illuminating the sample under conditions effective to cause: emitting of the first fluorescence emission band from the one or more viable cells dyed by the membrane-permeable fluorescent dye, emitting of the second fluorescence emission band from the one or more nonviable cells dyed by the membrane-impermeable fluorescent quenching dye, and quenching of at least a portion of fluorescence of the membrane-permeable fluorescent dye in the one or more nonviable cells by the membrane-impermeable fluorescent quenching dye; and selectively analyzing the sample for: a presence of the one or more viable cells according to the first fluorescence emission band and/or a presence of the one or more nonviable cells according to the second fluorescence emission band.

2. The method of claim 1, selectively analyzing the sample comprising detecting a number of the one or more viable cells present in the sample and a number of the one or more nonviable cells present in the sample.

3. The method of claim 1, wherein:
illuminating the sample comprises selectively illuminating in: the first excitation band corresponding to the membrane-permeable fluorescent dye and/or the second excitation band corresponding to the membrane-impermeable fluorescent quenching dye; and
selectively analyzing the sample comprises analyzing light emitted from the sample for the first fluorescence emission band and the second fluorescence emission band; and
further comprising distinguishing the one or more viable cells and/or the one or more nonviable cells according to a spectral difference between the first fluorescence emission band and the second fluorescence emission band.

4. The method of claim 1, selectively analyzing the sample comprising:
acquiring an image of the sample using light emitted by the first fluorescence emission band and the second fluorescence emission band; and
determining a number of the one or more viable cells in the image according to light emitted by the first fluorescence emission band, and a number of the one or more nonviable cells in the image according to light emitted by the second fluorescence emission band.

5. The method of claim 1, illuminating and selectively analyzing the sample comprising using one or more of: fluorescence imaging, fluorescence spectroscopy, fluorescence imaging microscopy, epifluorescence microscopy, confocal fluorescence imaging microscopy, a fluorometer, a fluorescence microplate reader, and fluorescence flow cytometry.

6. The method of claim 1, wherein the cell culture device comprises at least one of: a multiwell plate, a multiwell strip, an optical cell, and a flow cytometry apparatus.

7. The method of claim 1, further comprising culturing the one or more viable cells in the sample under cell culture conditions.

8. The method of claim 1, selectively analyzing the sample being conducted at two or more points in time to determine a presence or an absence of a change in a number of the one or more viable cells and/or a number of the one or more nonviable cells.

9. The method of claim 1, further comprising contacting the sample with at least one agent, selectively analyzing the sample comprising analyzing the one or more viable cells and/or the one or more nonviable cells for a presence or an absence of a change in response to the at least one agent.

10. The method of claim 9, wherein analyzing the presence or the absence of the response is characterized with respect to one or more of: an overall sample concentration, a concentration gradient in the sample, a time variation of the overall sample concentration, and a time variation of the concentration gradient in the sample.

11. The method of claim 9, the at least one agent comprising an anticancer agent, a therapeutic drug used as an adjunct in cancer therapy, and a compound suspected of modulating cancer therapy.

12. The method of claim 1, the sample comprising one of prokaryotic cells, eukaryotic cells, mammalian cells, human cells, cancer cells, primary tumor cells, primary tumor cells from a single human subject, or cells of a patient-derived cancer cell xenograft.

13. The method of claim 1, comprising one of:
contacting the sample with the membrane-permeable fluorescent dye before the membrane-impermeable fluorescent quenching dye;
contacting the sample with the membrane-permeable fluorescent dye after the membrane-impermeable fluorescent quenching dye;
contacting the sample with the membrane-permeable fluorescent dye at the same time as the membrane-impermeable fluorescent quenching dye; and
contacting the sample with a composition comprising the membrane-permeable fluorescent dye together with the membrane-impermeable fluorescent quenching dye.

14. The method of claim 1, the membrane-permeable fluorescent dye and the membrane-impermeable fluorescent quenching dye being nucleic acid binding dyes.

15. The method of claim 1, the amount of the membrane-impermeable fluorescent quenching dye being effective to substantially quench fluorescence of the membrane-permeable fluorescent dye in the one or more nonviable cells.

16. The method of claim 1, the first fluorescent emission band characterized by an overlap with an excitation band of the membrane-impermeable fluorescent quenching dye, the overlap being effective to provide the quenching of at least a portion of fluorescence of the membrane-permeable fluorescent dye in the one or more nonviable cells by the membrane-impermeable fluorescent quenching dye.

17. The method of claim 1, the membrane-permeable fluorescent dye being selected from Table I and the membrane-impermeable fluorescent quenching dye being selected from Table II.

18. The method of claim 1, the membrane-permeable fluorescent dye and the membrane-impermeable fluorescent quenching dye being a dye pair (a) or (b) selected from Table III.

* * * * *